US006039708A

United States Patent [19]

Schaming

[11] Patent Number: 6,039,708

[45] Date of Patent: Mar. 21, 2000

[54] FLEXIBLE CORD COLLAR HARNESS DEVICE

[76] Inventor: Michael J. Schaming, 82 Sands St., Staten Island, N.Y. 10304

[21] Appl. No.: 09/288,561

[22] Filed: Apr. 9, 1999

[51] Int. Cl.$^{7}$ ........................................................ A61F 5/00

[52] U.S. Cl. .................... 602/18; 128/845; 128/DIG. 23; 128/875

[58] Field of Search .................................... 128/845, 846, 128/DIG. 20, 869, 875; 602/5, 17, 18

[56] References Cited

U.S. PATENT DOCUMENTS

| | | | |
|---|---|---|---|
| 2,573,600 | 10/1951 | Pruehs | 174/153 |
| 4,034,747 | 7/1977 | Leroy | 602/18 |
| 4,167,301 | 9/1979 | Mundschenk | 339/105 |
| 4,757,554 | 7/1988 | Blair | 602/18 |
| 5,056,508 | 10/1991 | Brunell | 602/18 |
| 5,255,866 | 10/1993 | Campolo | 242/85.1 |
| 5,318,158 | 6/1994 | Seaholtz | 191/12 |
| 5,409,450 | 4/1995 | Donelson | 602/18 |
| 5,785,547 | 7/1998 | Cross et al. | 439/369 |

*Primary Examiner*—Michael A. Brown
*Attorney, Agent, or Firm*—Henderson & Sturm

[57] ABSTRACT

A collar harness device 10 to protect a user's neck and upper torso from frictional engagement with elongated flexible tubular items 100 such as pneumatic hoses and electrical cords wherein the device 10 includes a cape member 20 having an upper collar portion 21 dimensioned to receive a portion of a flexible tubular item 100 and a lower shroud portion 23 having wing elements 24, 25 which project outwardly from the collar portion 21 and a lower end that covers the upper portion of the user's spine wherein the cape member 20 is operatively connected to a portion of the user's clothing by a harness unit 12.

9 Claims, 1 Drawing Sheet

FLEXIBLE CORD COLLAR HARNESS DEVICE

BACKGROUND OF THE INVENTION

1. Field of the Invention

The present invention relates to the field of strain relief devices for electrical cords or the like and, in particular, to a device that allows a user to drape a cord around their neck in a low friction, comfortable fashion.

2. Description of Related Art

As can be seen by reference to the following U.S. Pat. Nos. 5,785,547; 5,318,158; 5,255,866; 4,167,301; and 2,573,600, the prior art is replete with flexible cord strain relief devices that are primarily focused on limiting stress on the cord per se.

While all of the aforementioned prior art constructions are more than adequate for the basic purpose and function for which they have been specifically designed, they are uniformly deficient with respect to their failure to provide a simple, efficient, and practical device that limits the stress and strain on a workman who has to deal on a regular basis with elongated electrical cords and/or pneumatic hoses.

As anyone who has had to deal on a regular basis with long electrical cords or pneumatic hoses is all too well aware, the manipulation of these elongated cords is extremely cumbersome and the loops of cord that are routinely generated under normal working conditions represents a serious work hazard not only because of the tripping potential but also due to the difficulty encountered in rolling other pieces of equipment over the cords.

In addition, to counter the cumulative weight of the elongated length of cord, most workmen have resorted to wrapping or draping a portion of the cord around their necks to facilitate the movement of the cord which results in undue frictional forces being exerted against the back of the workman's neck.

As a consequence of the foregoing situation, there has existed a longstanding need among workmen for a new and improved device that will allow the user to drape a portion of an elongated length of electrical cord or the like around their neck in the course of their tasks and to reduce the strain and friction on the user's neck as they maneuver the elongated length of cord; and, the provision of such a construction is the stated objective of the present invention.

BRIEF SUMMARY OF THE INVENTION

Briefly stated, the flexible cord collar harness device that forms the basis of the present invention comprises, in general, a collar unit that is dimensioned to surround at least a portion of the user's neck and a harness unit that is operatively connected to the collar unit and releasably engaging with the user's belt.

As will be explained in greater detail further on in the specification, the collar unit comprises a generally rigid miniature cape member having an upper collar portion and a lower shroud portion wherein the collar portion surrounds the back and a portion of the sides of the user's neck and is dimensioned to receive a portion of an elongated flexible tubular item such as a pneumatic hose or electrical cord; and, wherein the shroud portion has a pair of wing elements that project outwardly from the collar portion and a lower end which covers the upper portion of the user's spine.

In addition, the harness unit is operatively associated with the collar unit and includes a pair of suspender style strap members which are used to connect the device to the user's belt or pants and maintain the collar unit in the proper relationship relative to the user's neck.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
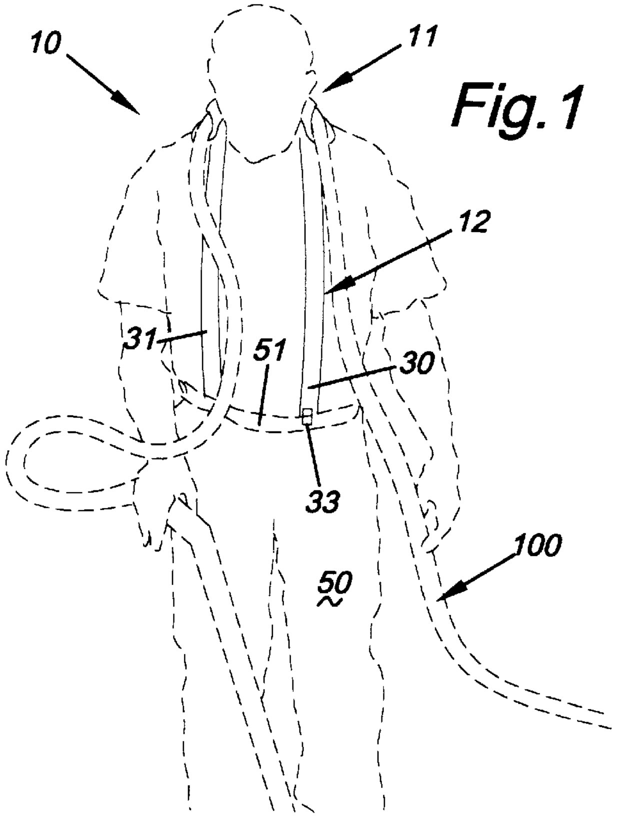
FIG. 1 is a perspective view showing the collar harness device being used with an elongated cord or hose.

As can be seen by reference to the drawings, and in particular to FIG. 1, the collar harness device for flexible hoses and electrical cords that forms the basis of the present invention is designated generally by the reference number 10. The collar harness device comprises, in general, a collar unit 11 and a harness unit 12. These units will now be described in seriatim fashion.

Figure 2:
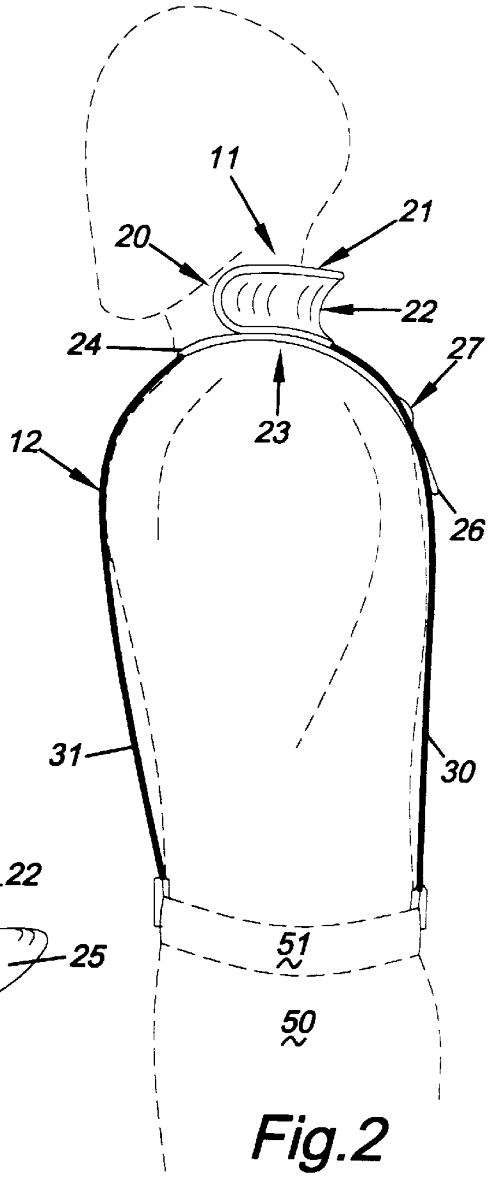
FIG. 2 is a side view of the device installed on a worker.
Figure 3:
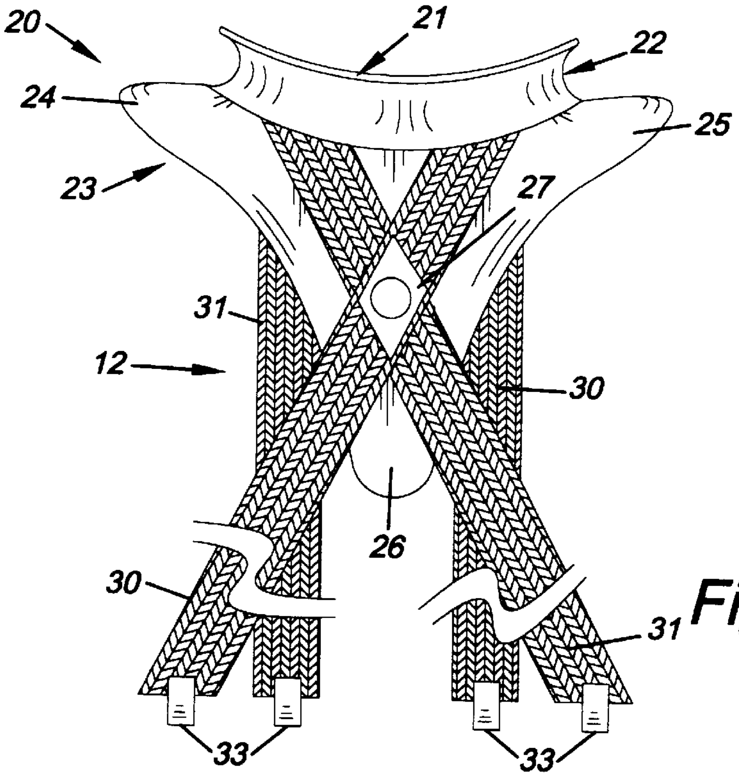
FIG. 3 is a rear view of the collar harness device.

As shown in FIGS. 2 and 3, the collar unit 11 comprises a generally rigid miniature cape member 20 having an upper collar portion 21 which partially surrounds the sides and completely surrounds the back of the user's neck; wherein, the collar portion 20 has a generally C-shaped cross-sectional configuration which defines an arcuate trough 22 whose opening is directed outwardly relative to the user's neck.

In addition, the miniature cape member 20 also has an arcuate, generally inverted triangular shaped lower shroud portion 23 which depends generally downwardly and outwardly from the bottom of the collar portion 21 wherein the upper end of the shroud portion 23 is flared outwardly to form wing elements 24, 25 and the lower end 26 of the shroud portion 23 is dimensioned to cover the upper portion of the user's spinal column and is further provided with an anchor element 27 whose purpose and function will be described presently.

As can best be appreciated by reference to FIG. 3, the harness unit 12 comprises a pair of elongated strap members 30 and 31, whose opposite ends are provided with fastening members 33 which are adapted to releasably engage the user's pants 50 or belt 51 in a suspender fashion wherein the intermediate portion 35 of the strap members 30, 31 are secured to one another in a criss-cross fashion and affixed to the collar unit 11 by the anchor element 27.

In use, the worker would don the device 10 similar to a pair of suspenders after they had positioned the collar unit 11 around the back of their neck as depicted in FIGS. 1 and 2. Then, when they were compelled to drape a portion of an elongated flexible tubular item such as a pneumatic hose or electrical cord designated generally as 100 around their neck, the portion of the flexible tubular item 100 that would normally be in contact with the back of their neck would rest within the arcuate trough 22 of the upper collar portion 21 of the cape member 20.

Furthermore, if one or more coils of the cord were draped around the user's neck while wearing this device, any slippage of the single or plural coils would contact the wing elements 24, 25 and the adjacent surrounding surfaces of the upper end of the shroud portion 23 of the collar unit 11.

In this manner, all direct contact of the cord coils with the neck and adjacent portions of the user's upper torso is eliminated and the portions of the cord 100 that would normally rub against the user's skin or clothing would slide on the relatively smooth surface of the collar unit 11.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooded parts together, whereas, a screw employs a helical surface, in the environment of fastening wooden parts, a nail and a screw may be equivalent structures.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A collar harness device to protect a user's neck and upper torso from frictional engagement with elongated flexible tubular items including pneumatic hoses and electrical cords wherein the device comprises:

a collar unit including a generally rigid cape member having a collar portion which surrounds the back and a portion of the sides of the user's neck; wherein, the collar portion defines an arcuate trough having an opening that is directed outwardly from the users neck and dimensioned to receive a portion of a selected one of said elongated flexible tubular items.

2. The device, as in claim 1, further comprising:

means for positioning and maintaining the collar portion of the cape member in a surrounding relationship relative to the user's neck.

3. The device, as in claim 1; wherein, the rigid cape member further includes a shroud portion attached to said collar portion and having an upper end provided with outwardly extending wing elements.

4. The device, as in claim 3; wherein, said wing elements have an arcuate configuration.

5. The device, as in claim 4; wherein, said shroud portion has a lower end which is dimensioned to cover the upper portion of the user's spinal column.

6. The device, as in claim 5; further comprising:

a harness unit operatively associated with the collar unit and including a pair of elongated strap members provided with fastening members on their opposite ends.

7. The device, as in claim 6; wherein, the strap members are operatively connected to the shroud portion of the cape member.

8. The device, as in claim 7; wherein, the strap members are further connected to one another.

9. The device, as in claim 8; wherein, the strap members connected to one another and the shroud portion of the cape member at the same location.

* * * * *